United States Patent [19]

Baucom

[11] 4,195,631
[45] Apr. 1, 1980

[54] FLOW REGULATING DEVICE USEABLE IN PLASMA PHERESIS

[76] Inventor: Keith K. Baucom, 40 Abbey Ct., Ramsey, N.J. 07446

[21] Appl. No.: 915,389

[22] Filed: Jun. 14, 1978

[51] Int. Cl.² .............................................. A61M 5/00
[52] U.S. Cl. .......................... 128/214 R; 128/214.2; 128/274; 138/46; 137/625.15; 137/625.41; 137/625.46; 251/206
[58] Field of Search ............... 128/214 R, 227, 214.2, 128/274; 138/45, 45 A, 46; 251/208, 206, 210; 137/625.46, 625.41, 625.14

[56] References Cited

U.S. PATENT DOCUMENTS

| 37,786 | 2/1863 | Guernsey | 137/625.46 |
|---|---|---|---|
| 1,128,445 | 2/1915 | Henning | 138/45 A |
| 2,631,003 | 3/1953 | Heinz | 137/625.14 |
| 2,854,027 | 9/1958 | Kaiser et al. | 137/625.41 |
| 2,891,579 | 6/1959 | Burkland et al. | 138/45 |
| 3,385,321 | 5/1968 | Ehrens et al. | 137/625.46 |
| 3,730,170 | 5/1973 | Michael | 128/214 R X |
| 3,782,382 | 1/1974 | Naftulin et al. | 128/214 R |
| 3,837,360 | 9/1974 | Bubyla | 137/625.46 |
| 3,886,937 | 6/1975 | Bobo et al. | 128/214 R |
| 3,963,024 | 6/1976 | Goldowsky | 128/214 F X |

Primary Examiner—Henry K. Artis

[57] ABSTRACT

A liquid flow regulating device which is particularly useful in the process of plasma pheresis. The regulating device includes a hollow member communicating with a donor through a tube passing through one end of the hollow member. There is a liquid flow control member having a passageway therethrough closing the other end of the hollow member. A dial member rotatably mounted with respect to the flow control member. At least two passageways through said dial member adapted to be aligned with said passageway in the control member. Selection means on said dial member and said control member for positively positioning said control member passageway with one of said dial member passageways to control the liquid flow.

10 Claims, 8 Drawing Figures

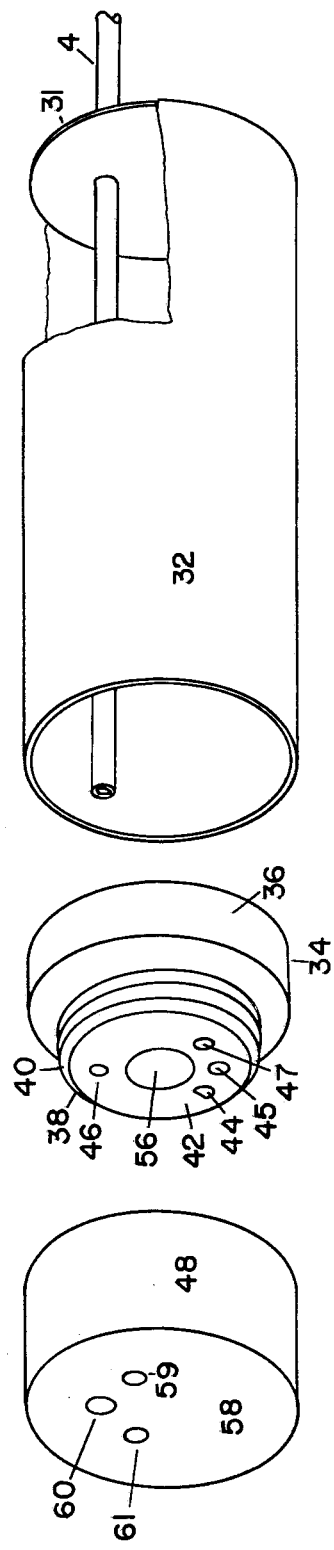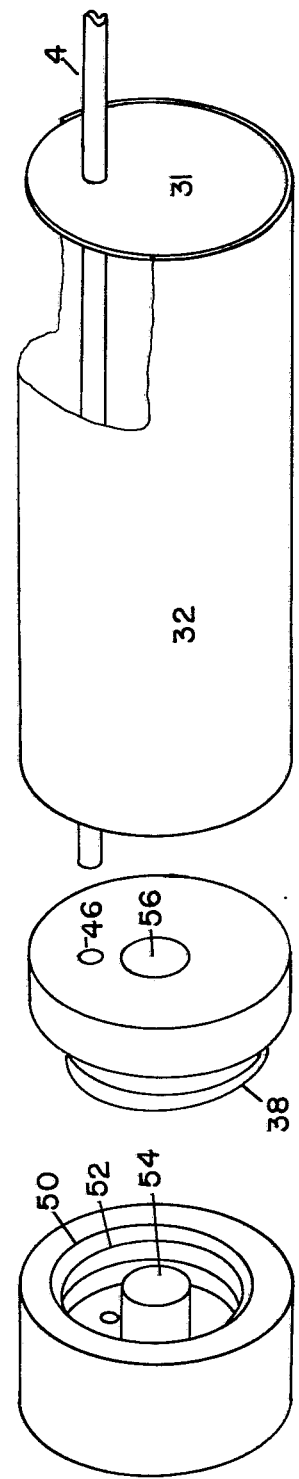

FLOW REGULATING DEVICE USEABLE IN PLASMA PHERESIS

This invention relates to a flow regulating device and more particularly to a device for selectively controlling the flow of saline, whole blood and red blood cells.

There is known in the medical art a process called plasma pheresis. Broadly speaking, in this process a quantity, e.g., 500 milliliters of whole blood is removed from the patient, the red blood cells separated from the plasma and then the red blood cells are turned to the donor. This procedure can then be repeated with the same donor. The purpose of this procedure is to separate the red blood cells from the remainder of the cellular elements. The cellular elements can be transferred to a patient in need thereof or subjected to testing.

In the plasma pheresis process saline is dripped to the patient to clear the tubes and remove any air in the tubes. A unit of whole blood is then removed from the donor and centrifuged so that the red blood cells separate from the plasma. During this latter step saline is fed to the patient. The red cells are returned to the donor through a filter. Thereafter, another unit of whole blood is removed from the patient, centrifuged to separate the red blood cells, while saline is fed to the patient, and then the red blood cells are returned through a filter to the donor.

One of the advantages of plasma pheresis is that a donor can make two donations twice a week whereas the normal time lapse between single donations of whole blood is eight (8) weeks.

The plasma pheresis process is accomplished in the prior art by the use of at least three (3) plastic bags or glass bottles. There are two bags for whole blood, which are also used for returning the red cells to the donor, and one saline bag. In other words, the bag used to collect the whole blood is the same bag in which the red cells only are located before being returned to the donor since the plasma has been removed from the whole blood leaving only the red cells in the bag. Each of the bags is connected to tubing for communication to the patient.

The operation of this prior art device and method is satisfactory. However, numerous pieces of auxiliary equipment are required such as clips, clip sealers, multiple hemostats, two pair of scissors, and hand clamps. Moreover, the operator of the system must apply the clamps, ets., at precisely the correct time to prevent through drippage blood loss and saline loss. It is also necessary to avoid blood clots and to prevent air from entering the system. Should the latter events occur, of course, the patient could be in severe danger. Another disadvantage of the prior art systems is that they invariably include a "Y" connection. The use of a "Y" connection presents a potentially dangerous situation in that there is a possibility of blood clots forming in the "Y" which, if directed to the donor, is potentially fatal. The prior art systems may also become contaminated.

In short, the prior art system requires a great many auxiliary parts and a certain amount of skill to use these elements properly and at the correct time.

Briefly described, the present invention relates to a flow regulating device. In one form the device is particularly adapted to control the flow of whole blood, saline and red blood cells in the process of plasma pheresis. The flow regulating device is at least a two and possibly a three part construction one of which is rotatable with respect to the other part or parts.

The stationary part has a single aperture through which liquid is adapted to flow in a straight line and this aperture can be directly aligned with one of several apertures in the rotatable member to permit straight line or laminar flow of the liquid. This is particularly important where the liquid is blood since it prevents clotting which could have serious consequences for the donor.

The stationary member and rotatable member further includes cooperating indentations or dimples and a mating protuberance or bump to cause alignment of the passageway through the stationary member with a selected one of the several passageways in the rotatable member to thereby control the flow of liquid as desired. In each instance, however, the flow is laminar, i.e. in a straight line. Further, the device is constructed so that there is an automatic cut-off of liquid by mis-aligning the bump and the indentations.

The flow regulating device of this invention is constructed so that a portion of the stationary member can serve as a hand pump which assists causing the liquid to flow.

One embodiment of the flow control device of this invention is used for plasma pheresis and another embodiment can be used for whole blood collection and for blood sample collection.

The invention consists of the novel parts, steps, constructions and improvements shown and described.

OBJECTS

In view of the foregoing it is an object of this invention to provide a new and improved liquid flow regulating device which is particularly adapted for controlling the flow of blood or its components.

A further object of this invention is to provide a new and improved liquid regulating device which causes laminar or straight-through flow which makes such device particularly useful in controlling the flow of blood.

A further object of this invention is to provide a liquid regulating device which is particularly useful in the process of plasma pheresis.

A still further object of this invention is to provide a new and improved liquid regulating device for controlling the flow of whole blood, saline, and red blood cells by a turning movement of one part with respect to another part.

A further object of this invention is to provide a blood regulating device including a dial mechanism adapted to direct a single flow through one of a plurality of passageways.

A further object of this invention is to provide a blood flow control device having indicia for identifying the passageway through which the liquid flows.

Another object of this invention is to provide a system for plasma pheresis.

Additional objects and advantages of this invention will be set forth in the description which follows and, in part, will be obvious from the description. The objects and advantages being realized and obtained by means of the instrumentations, parts, and apparatus, being particularly pointed out in the appended claims.

The accompanying drawings which are incorporated in and constitute part of this specification illustrate an embodiment of the invention and together with the description serve to explain the principles of the invention.

OF THE DRAWINGS

FIG. 2 is a perspective view of the liquid regulating devide of this invention.

FIG. 3 is another perspective view of the liquid regulating device of this invention.

DETAILED DESCRIPTION OF THE INVENTION

Figure 1:
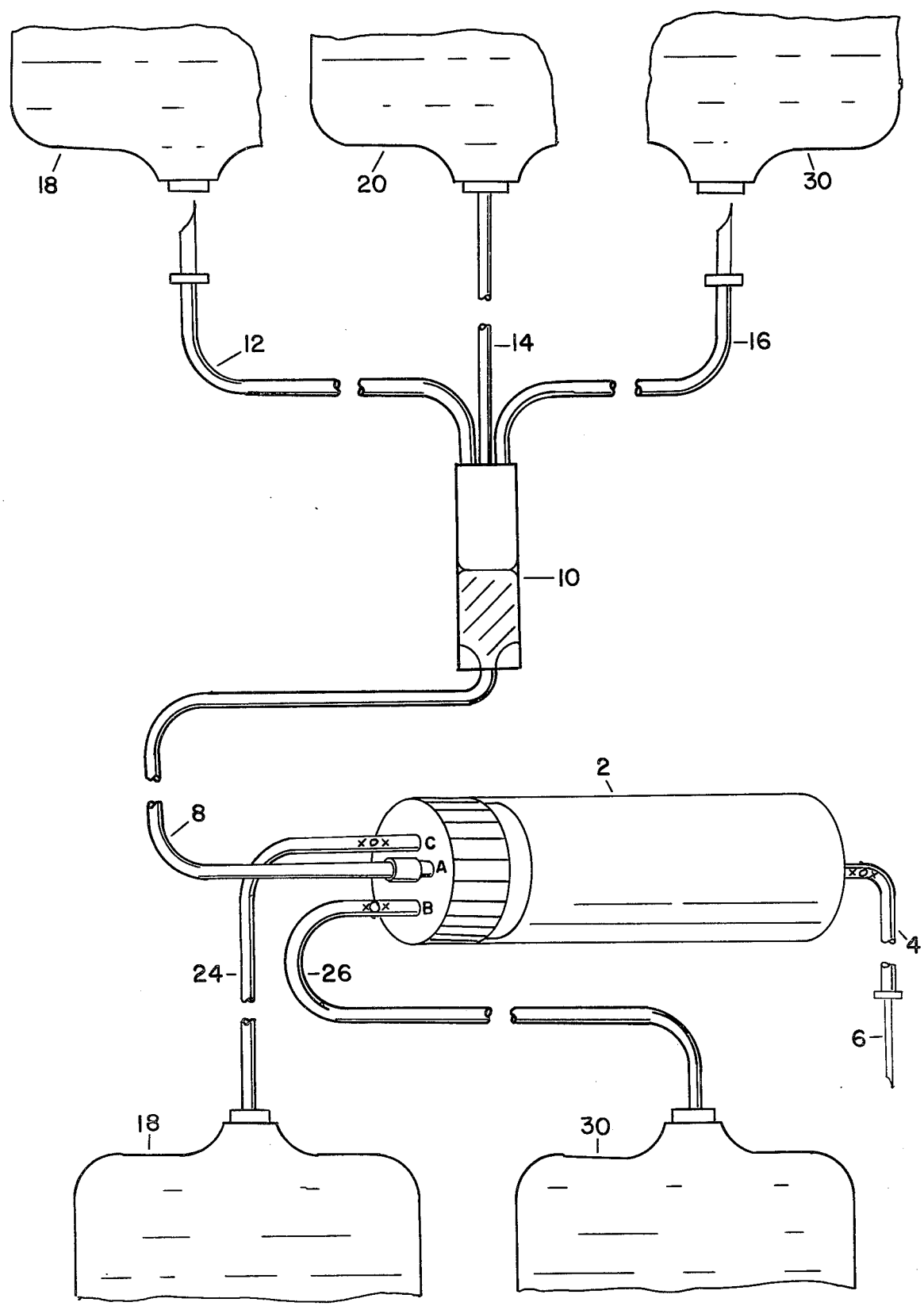
FIG. 1 is a plan view showing the liquid regulating device of this invention and its environmental use.
Figure 4:
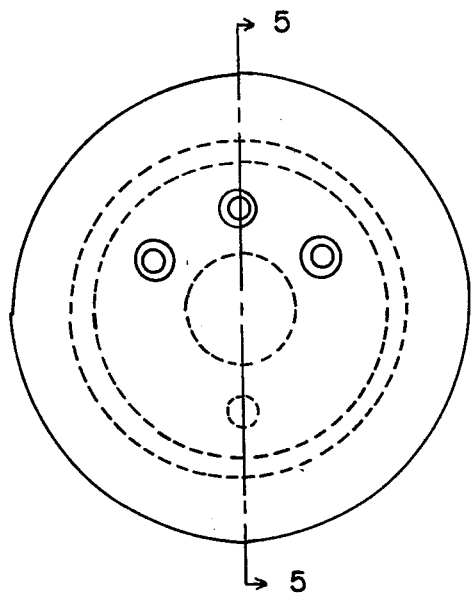
FIG. 4 is a plan view of one of the parts of the liquid regulating device.

In FIG. 1 there is shown the overall system and the flow regulating assembly 2 of this invention in its operative position.

Extending from one end of the flow regulating device 2 is a tube 4 having attached thereto a conventional needle 6 adapted to be inserted into the donor in the usual manner.

Extending from the other end of the flow regulating assembly 2 is a tube 8 connected to a conventional blood filter 10. There are three tubes 12, 14 and 16 adapted to be connected to the container which may be in the form of bags or containers 18, 20 and 30 respectively. Extending from the same end of the flow regulating assembly 2 as the tube 8 are tubes which are adapted to be connected to the containers 18 and 30 respectively which also can be in the form of bags or containers.

It will be understood, however, that not all of the containers shown in FIG. 1 will be in operational use at the same time. Indeed, it will be noted that bags 18 and 30 are shown in two positions, this is because at one time these bags contain whole blood and at another time, after plasma has been removed, they contain red blood cells only.

The flow regulating assembly is best shown in FIGS. 2-7. As shown, the flow regulating assembly 2 consists of three basic elements.

There is a hollow generally cylindrical member 32 having the tube 4 extending into the interior through wall 31. The other end of the cylindrical member is open. The cylindrical member 32 is of a size such that it can comfortably fit within the donor's hand. When in use the donor's hand grasps and regrasps the cylindrical member 32 so as to "pump" blood from the donor. Such a pumping action decreases the amount of time required to remove the blood from the donor.

The second element of the flow regulating assembly 2 is a liquid flow control member 34. The liquid flow control member 34 could, if desired, be integral with the hollow cylindrical member 32. The liquid flow control member has a boss 36 which fits within the open end of the hollow cylindrical member with a tight friction fit so that there is no relative movement between these two parts.

The liquid flow control member includes a reduced diameter portion 38 having a series of radially outwardly extending ridges 40 the purpose of which will be explained.

The surface 42 of the liquid control member furthest from the hollow cylindrical member has a plurality and preferably three indentations or dimples 44, 45 and 47 which assist in controlling the flow of liquid through the flow regulating assembly 2. Extending entirely through the fluid member is a passageway 46 which is in communication with the tube 4.

Figure 5:
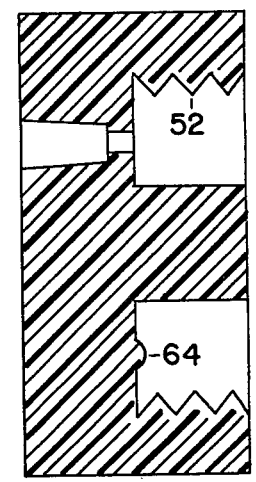
FIG. 5 is a sectional view taken along line 5—5 of FIG. 4.
Figure 6:
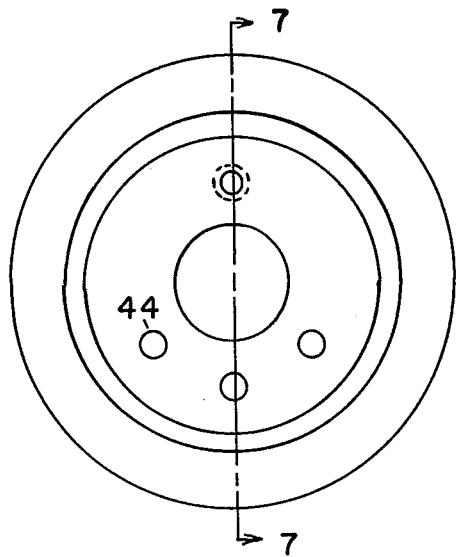
FIG. 6 is a plan view of another part of the liquid regulator device.
Figure 7:
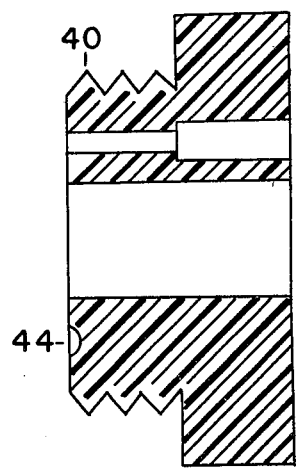
FIG. 7 is a sectional view taken along line 7—7 of FIG. 6. ;p

The third member of the flow regulating assembly is a dial mechanism 48. The dial mechanism includes a hollowed out portion 50 the inner surface of which has a plurality of radially inwardly extending ridges 52. The ridges 52 are adapted to cooperate with the ridges 40 on the flow regulating member so that these parts are hold together against longitudinal separation while at the same time are relatively rotatable. If desired, the dial mechanism can include a male member 54 adapted to fit within the female opening 56 in the flow control member 36. The dial mechanism is closed at one end by wall 58, the inner surface of which has a detent or protuberance 64 (FIG. 5). The detent 64 is adapted to fit within one of the three dimples 44 as will become apparent.

Extending entirely through the wall 58 are a plurality of passageways 59, 60 and 61. As shown, passageway 60 communicates with tube 8, passageway 61 communicates with tube 24 and passageway 59 communicates with tube 26. The dial mechanism, detent and dimples form a selection means for determining the path of liquid flow.

As shown in FIG. 1 the outer wall 58 can be marked with indicia such as A, B, C. so that the operator can tell which tube will be in operation. The arrangement is such that if the detent 64 is not in engagement with any of the dimples 44, 45 and 47 there will be no fluid passing through the flow regulating assembly. This provides an automatic cut-off of liquid flow.

It will be noted that the flow of liquid through the flow regulating device of this invention is laminar, i.e. straight, thus substantially reducing the possibility of blood clots forming which could be potentially fatal to the donor.

OPERATION

Referring to FIG. 1 a typical use of the device of the flow regulating device would be as follows.

The needle 6 is inserted into the donor and the dial mechanism turned to portion A so that saline solution is passed from container 20 through tube 14, filter 10, tube 8 through the liquid regulating device 2 to the tube 4 and thence to the donor. After a period of time the dial mechanism 48 is turned to position B thus stopping saline flow. At this time the donor grasps and regrasps the hollow cylindrical member 32 so that whole blood will pass through the hollow cylindrical member 32 into tube 26 leading to collection bag 30.

When the collection bag 30 is filled the dial mechanism is again turned to a position between A and B to stop the flow of blood. The dial is then turned to position A and saline directed to the donor. The whole blood contents of collection bag 30 are then centrifuged to separate the red blood cells from the other blood components. The red blood cells remain in bag 30 after the plasma has been removed. The dial mechanism is turned to position A, tube 16 is attached to bag 30 so that the red blood cells flow through tube 16, filter 10, line 8, flow regulating device 2 and thence to the donor.

This entire process can then be repeated by using tube 24 with the dial turned to position C so that whole blood flows to bag 18.

The use of the simple dial mechanism to control the flow of liquid, i.e. saline, whole blood and red blood cells is much simpler than the conventional method of using numerous clamps, etc. to control the liquid flow.

The flow regualting device of this invention is also safer because the flow of liquid is laminar, i.e. straight, thus reducing the possibility of blood clots, blood drippage or contamination.

Figure 8:
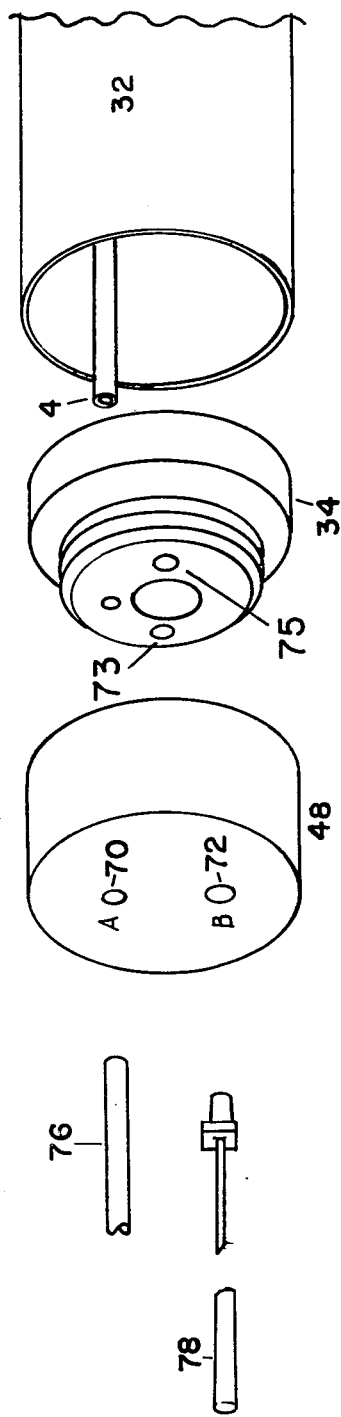
FIG. 8 is an exploded view of another embodiment of the invention.

Another embodiment of the invention is shown in the exploded view of FIG. 8. As in the case of the embodiment shown in FIGS. 1-7, this embodiment includes a hollow cylindrical member 32, a liquid flow control member 34 and a dial mechanism 48. These parts are assembled so that the dial mechanism 48 is rotatable with respect to the liquid flow control member 34 while these parts were longitudinally immovable. This is accomplished as in the embodiment of FIG. 1-7. Also, in this case, the dial mechanism 48 has indicia A and B to indicate the passageway in communication with passageway 46. The dial mechanism in this embodiment has only two openings and the liquid flow control member has only two indentations or dimples 73, 75 adapted to cooperate with a single bump or protuberance (not shown) in the same manner as in the firm embodiment. The liquid flow control member 34 has a single passageway 46 therethrough which communicates with tube 4 which communicates with the donor as in the embodiment of FIGS. 1-7.

The passageway 70, FIG. 8, is adapted to be attached to tubing 76 leading to a collection container for whole blood (not shown). The passageway 72 is adapted to be connected to a needle which after cover 78 is removed can be placed in a vacuum type test tube so that sample quantities of whole blood can be withdrawn from the donor for testing and the like.

OPERATION

In use, passageway 70 is dialed into alignment with passageway 46 so that whole blood goes through tube 4 exits tube 76 into a collection container. When it is desired to sample the blood in the collection container, the dial mechanism 48 is tuned so that the passageway 72 and its needle is aligned with passageway 46 so that when the needle is placed in a vacuum tube so that blood will be drawn into the test tube from the collection container which is now connected to the tube 4.

What is claimed is:

1. A liquid flow regulating device adapted to control the flow of blood and other liquids comprising:
   (a) a hollow member with one end closed having tube means extending through said closed end to communicate liquid to and from a donor;
   (b) a liquid flow control member closing the other end of said hollow member there being a passageway for the flow of liquid through said liquid flow control member;
   (c) a dial member in engagement with said blood control member so as to be rotatable with respect thereto;
   (d) at least two passageways extending through said dial mechanism for the passage of liquid;
   (e) selection means of said dial mechanism and on said blood control member for positively selectively aligning one of said dial mechanism passageways and said liquid flow control member passageway; and
   (f) means for conducting liquid to and from said dial mechanism passageway; and
   (g) said hollow member, said dial member, said control member and the passageways thereto through being constructed and arranged for straight-line liquid flow.

2. A liquid flow regulating device as defined in claim 1 wherein said dial mechanism has at least three passageways therethrough so that liquid can selectively be directed to and from a plurality of chambers in communications with said passageways and wherein said selection means can align any one of said plurality of passageways in said dial mechanism with said liquid flow control member passageway or position said dial mechanism so that said blood control member passageway is misaligned with respect to all of said dial mechanism passageways thereby preventing liquid flow.

3. A device as defined in claim 1 wherein said selection means consists of a projection and at least one indentation whereby when said projection fits within said indentation said passageway in said dial member is aligned with said passageway in said control member.

4. A device as defined in claim 1 wherein said control member and said dial member have cooperating ridges which prevent relative longitudinal movement and permit relative rotative movement.

5. A device as defined in claim 4 wherein said hollow member has a length about the same as the width of an average adult's hand.

6. A device as defined in claim 4 wherein said dial member has three passageways therethrough.

7. A device as defined in claim 5 wherein said dial member had indicia adjacent the exit of each passageway identifying which passageway is in communication with the passageway through said control member.

8. A device as defined in claim 4 wherein said dial member has two passageways therethrough.

9. A system for plasma pheresis comprising:
   (a) a hollow member having a closed wall with a tube extending therethrough and adapted to be in communication with a donor;
   (b) a control member closing the other end of said hollow member and having a passageway therethrough;
   (c) a dial member and means attaching said dial member to said control member so that said dial member is rotatable with respect to said control member and said dial member and said control member are relatively longitudinally immovable;
   (d) at least three passageways through said dial member adapted to be aligned with said passageway in said control member;
   (e) said dial member and said control member having a cooperating projection and at least three indentations to positively align one of said passageways in said dial member with said passageways in said control member;
   (f) means for directing saline through a first of said passageways in said dial member through said control member and hollow member to a donor;
   (g) means for thereafter stopping the flow of saline and for directing whole blood from the donor through a second passageway in said dial member to a collection chamber;
   (h) means for thereafter stopping the flow of whole blood and directing red blood cells through said first passageway to the donor;
   (i) means for stopping the flow of red blood cells and then directing the flow of whole blood from the donor through a third passageway in said dial member to a collection chamber; and
(j) means for stopping the flow of whole blood and for directing the flow of red cells to the donor.

10. A system for plasma pheresis comprising:
(a) means for filtering saline and red cells;
(b) means for supplying saline to said filter;
(c) tube means adapted to be connected to a supply of red blood cells and communicating with said filter;
(d) a flow regulating device;
(e) tube means leading from said filter to a first passageway in said flow regulating device;
(f) first and second containers;
(g) second and third passageways in said flow regulating device;
(h) first and second containers and tube means leading from said second and third passageways to said first and second containers;
(i) said flow regulating device having:
  (1) a hollow member one end having tube means communicating with a donor,
  (2) means at the other end of said hollow member forming a pasateway leading to the interior of said hollow member,
  (3) a dial member rotatably mounted with respect to said hollow member,
  (4) means forming three passageways through said dial member, and
  (5) means for selectively and positively aligning said three passageways in said dial member with said passageway leading to the interior of said hollow member.

* * * * *